United States Patent
Morimoto et al.

(10) Patent No.: US 9,274,033 B2
(45) Date of Patent: Mar. 1, 2016

(54) SUBSTRATE-SHEET FABRICATING METHOD

(71) Applicant: OLYMPUS CORPORATION, Tokyo (JP)

(72) Inventors: Nobuhiko Morimoto, Tokyo (JP); Jun Funazaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 43 days.

(21) Appl. No.: 14/069,521

(22) Filed: Nov. 1, 2013

(65) Prior Publication Data

US 2014/0080174 A1 Mar. 20, 2014

Related U.S. Application Data

(63) Continuation of application No. PCT/JP2012/062606, filed on May 17, 2012.

(30) Foreign Application Priority Data

May 20, 2011 (JP) ................................ 2011-113361

(51) Int. Cl.
  *G01N 21/75* (2006.01)
  *G01N 1/28* (2006.01)
(52) U.S. Cl.
  CPC .............. *G01N 1/2813* (2013.01); *G01N 1/286* (2013.01); *G01N 2001/2873* (2013.01)
(58) Field of Classification Search
  CPC ...................... G01N 2001/2873; G01N 1/2813
  See application file for complete search history.

(56) References Cited

U.S. PATENT DOCUMENTS

| | | | |
|---|---|---|---|
| 3,448,510 A * | 6/1969 | Johnson, Jr. et al. | 29/413 |
| 3,932,220 A | 1/1976 | Liotta | |
| 4,647,543 A | 3/1987 | Stöcker | |
| 4,752,347 A | 6/1988 | Rada | |
| 5,356,751 A | 10/1994 | Cairncross | |
| 5,998,129 A | 12/1999 | Schutze et al. | |

(Continued)

FOREIGN PATENT DOCUMENTS

| | | |
|---|---|---|
| EP | 2 579 019 A1 | 4/2013 |
| JP | S48-13260 B1 | 4/1973 |

(Continued)

OTHER PUBLICATIONS

Extended Supplementary European Search Report dated Nov. 4, 2014 from related European Application No. 12 78 8956.6.

(Continued)

*Primary Examiner* — Jyoti Nagpaul
(74) *Attorney, Agent, or Firm* — Scully, Scott, Murphy & Presser, PC

(57) ABSTRACT

A group of small pieces of divided base substrate is arrayed on a sheet without gaps therebetween by means of a simple method. Provided is a substrate-sheet fabricating method including cutting into a group of small pieces a base substrate whose first-side surface is attached to a first sheet member; transferring the group of small pieces to a second sheet member by attaching the second sheet member, which can be contracted in the direction along a surface thereof, to second-side surfaces of the group of small pieces and by peeling off the first sheet member from the first-side surfaces of the group of small pieces; and making the second sheet member contract in the direction along the surface thereof.

17 Claims, 6 Drawing Sheets

(56) References Cited

U.S. PATENT DOCUMENTS

| | | |
|---|---|---|
| 2002/0142412 A1 | 10/2002 | Ogawa et al. |
| 2002/0197770 A1 | 12/2002 | Irie |
| 2003/0032082 A1 | 2/2003 | Leclerc |
| 2004/0014205 A1 | 1/2004 | Banes |
| 2006/0121596 A1 | 6/2006 | Chaumat |
| 2010/0050838 A1 | 3/2010 | Noguchi et al. |

FOREIGN PATENT DOCUMENTS

| | | | |
|---|---|---|---|
| JP | S55-086173 A | 6/1980 |
| JP | H10-229097 A | 8/1998 |
| JP | 11-148887 A | 6/1999 |
| JP | H11-163006 A | 6/1999 |
| JP | 2000-504824 A | 4/2000 |
| JP | 2002-202229 A | 7/2002 |
| JP | 2002-286592 A | 10/2002 |
| JP | 2003-7652 A | 1/2003 |
| JP | 2003-152056 A | 5/2003 |
| JP | 2003-521685 A | 7/2003 |
| JP | 2004-537712 A | 12/2004 |
| JP | 2005-34058 A | 2/2005 |
| JP | 2005-335020 A | 12/2005 |
| JP | 2006-158394 A | 6/2006 |
| JP | 3786711 B2 | 6/2006 |
| JP | 2008-286528 A | 11/2008 |
| JP | 2009-44123 A | 2/2009 |
| JP | 2009-260226 A | 11/2009 |
| JP | 2010-074135 A | 4/2010 |
| WO | 02/37944 A2 | 5/2002 |
| WO | 2008/053916 A | 5/2008 |
| WO | 2010/119361 A1 | 10/2010 |

OTHER PUBLICATIONS

English Abstract only of DE 10003588 A1, dated Aug. 2, 2001.
English Abstract only of WO 9835216 A1, dated Aug. 13, 1998.
International Search Report dated Jul. 10, 2012 issued in PCT/JP2012/062606.
Leica Microsystems, "Leica LMD 7000", p. 2, together with an English language translation.
International Search Report dated Jan. 29, 2013 from related International Application No. PCT/JP/2012/080106, together with an English language translation.
International Search Report dated Jun. 21, 2011 from related International Application No. PCT/JP/2011/062069, together with an English language translation.
U.S. Office Action dated Jul. 14, 2014 received in related U.S. Appl. No. 13/686,296.
U.S. Office Action dated Oct. 17, 2013 received in related U.S. Appl. No. 13/686,296.
U.S. Office Action dated May 17, 2013 received in related U.S. Appl. No. 13/686,296.
Extended Supplementary European Search Report dated May 29, 2015 from related European Application No. 12 85 1303.3.

* cited by examiner

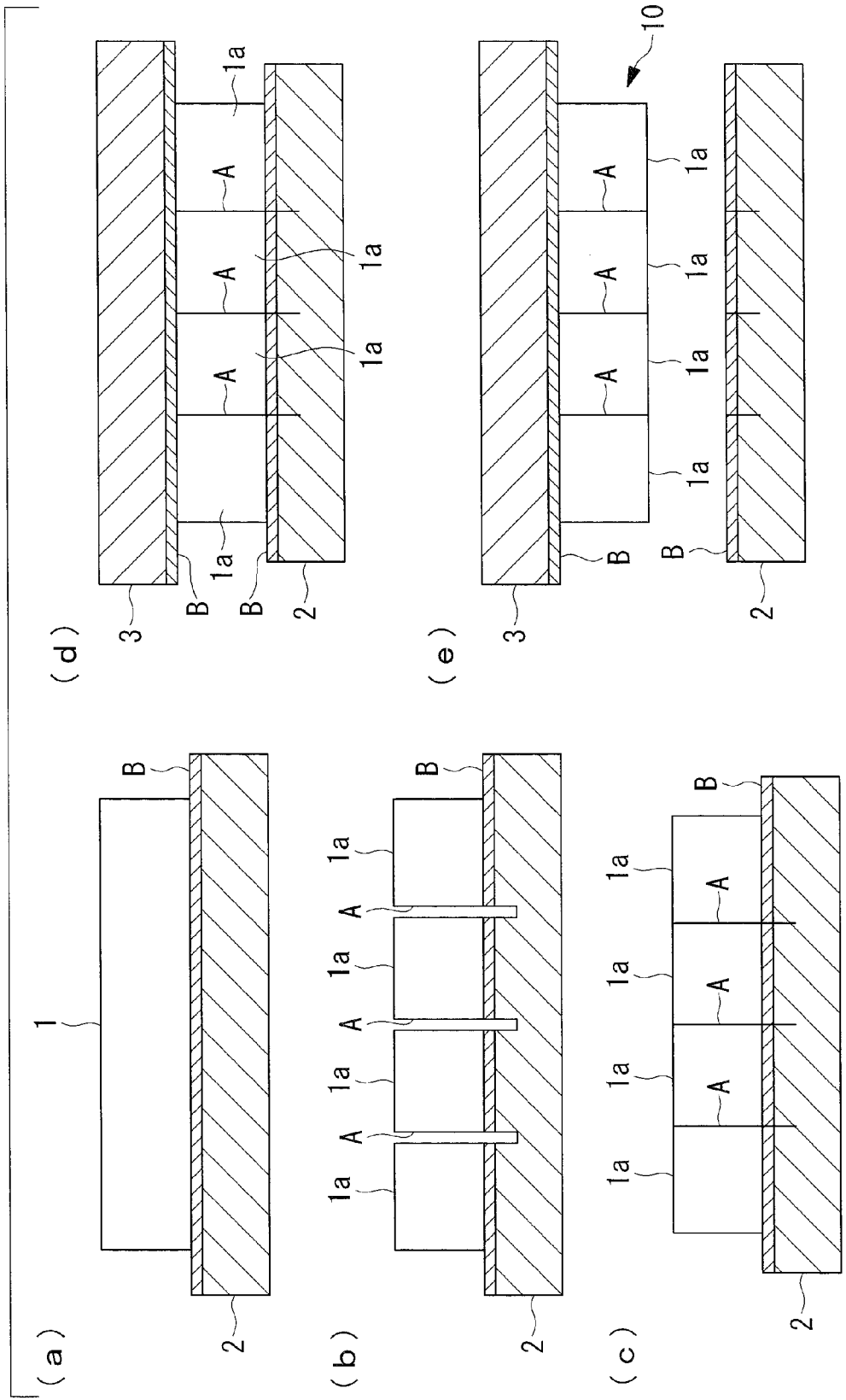

SUBSTRATE-SHEET FABRICATING METHOD

CROSS-REFERENCE TO RELATED APPLICATIONS

This is a continuation of International Application PCT/JP2012/062606, with an international filing date of May 17, 2012, which is hereby incorporated by reference herein in its entirety. This application claims the benefit of Japanese Patent Application No. 2011-113361, the content of which is incorporated herein by reference.

TECHNICAL FIELD

The present invention relates to a method of fabricating a substrate sheet, in particular, a substrate sheet for dividing a thin section of biological tissue to obtain very small segments thereof.

BACKGROUND ART

In the related art, there is a known microdissection method in which very small segments are cut out from a tissue section in order to perform tests of localized gene expression or the like in the tissue section (for example, see Patent Literature 1). The method of Patent Literature 1 requires large-scale equipment and well-developed skills.

On the other hand, there is a method employed as a similar method to that of Patent Literature 1, in which a base substrate such as a cover glass or the like is divided into a group of small pieces in advance; in this state, they are attached to an adhesive sheet that can be expanded, so as to be arrayed without gaps therebetween; a tissue section is attached on the group of small pieces; and the sheet is expanded to separate the small pieces from each other, thereby dividing the tissue section into segments along the outline of the individual small pieces. Here, the base substrate is manually divided by using a glass cutter in a state in which it is attached to the adhesive sheet, and thus, the group of small pieces are arrayed on the adhesive sheet without gaps therebetween. To divide the base substrate by using a glass cutter, first, grid-like grooves with spaces of several millimeters or less therebetween are made on the base substrate by using a glass cutter, and, subsequently, the base substrate is manually divided into small pieces along the grooves.

CITATION LIST

Patent Literature

{PTL 1} Publication of Japanese Patent No. 3786711

SUMMARY OF INVENTION

A first aspect of the present invention is a substrate-sheet fabricating method comprising: cutting into a group of small pieces a base substrate whose first-side surface is attached to a first sheet member; after the cutting the base substrate, transferring the group of small pieces to a second sheet member by attaching the second sheet member, which can be contracted in the direction along a surface thereof, to second-side surfaces of the group of small pieces and by peeling off the first sheet member from the first-side surfaces of the group of small pieces; and after the transferring the group of small pieces, making the second sheet member contract in the direction along the surface thereof.

A second aspect of the present invention is a substrate-sheet fabricating method comprising: cutting into a group of small pieces a base substrate whose first-side surface is attached to a first sheet member that can be contracted in the direction along a surface thereof; after the cutting the base substrate, making the first sheet member contract in the direction along the surface thereof; and after the making the first sheet member contract, transferring the group of small pieces to a second sheet member by attaching the second sheet member to second-side surfaces of the group of small pieces and by peeling off the first sheet member from the first-side surfaces of the group of small pieces.

A third aspect of the present invention is a substrate-sheet fabricating method comprising: cutting into a group of small pieces a base substrate whose first-side surface is attached to a first sheet member that can be contracted in the direction along a surface thereof; and after the cutting the base substrate, making the first sheet member contract in the direction along the surface thereof.

BRIEF DESCRIPTION OF DRAWINGS

FIG. 2 is schematic diagrams of steps in the substrate-sheet fabricating method in FIG. 1, respectively showing (a) a state in which a base substrate is attached to a contractible sheet, (b) a state in which the base substrate is cut into a group of small pieces, (c) a state in which the contractible sheet is made to contract, (d) a state in which the group of small pieces are attached to an expandable sheet, and (e) a state in which the group of small pieces are transferred to the expandable sheet.

DESCRIPTION OF EMBODIMENT

A substrate-sheet fabricating method according to an embodiment of the present invention will be described below with reference to the drawings.

Figure 1:
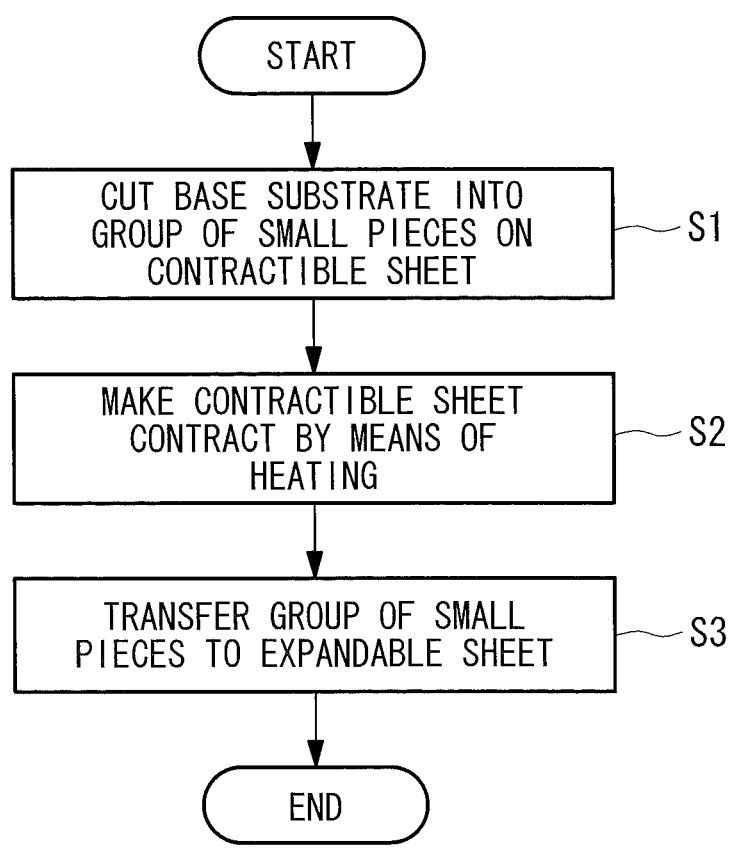
FIG. 1 is a flowchart showing a substrate-sheet fabricating method according to an embodiment of the present invention.

As shown in FIG. 1, the substrate-sheet fabricating method according to this embodiment includes a cutting step S1 in which a flat-plate-like base substrate 1, where one tissue section can be attached on a first-side surface thereof, is cut on a contractible sheet (first sheet member) 2; a contracting step S2 in which the contractible sheet 2 is made to contract; and a transferring step S3 in which the cut base substrate 1 is transferred to an expandable sheet (second sheet member) 3 from the contractible sheet 2.

As shown in (a) of FIG. 2, the cutting step S1 is performed by cutting the base substrate 1, in the state in which the first-side surface thereof is attached to a surface of the contractible sheet 2, into a group of small pieces 1a that are like cubes having substantially identical sizes. Here, a cutting device used to cut a wafer in the semiconductor fabricating process, such as a dicer, is used to cut the base substrate 1. By doing so, as shown in (b) of FIG. 2, the group of small pieces 1a is left on the contractible sheet 2 in the orderly arranged state, and gaps A having a width in accordance with the thickness of the blade of the cutting device are formed between the small pieces 1a.

It is preferable that the size of each side of the small pieces 1a be a suitable size for manipulation in gene analysis or the like, for example, about 0.1 mm to 5 mm, which allows them to be accommodated in individual wells of a microplate. The base substrate 1 should have a thickness that can easily be cut by a cutting device and that also allows easy handling, and it is preferable that the thickness be about 0.05 mm to 0.5 mm.

A substrate formed of a material that can be cut relatively easily by the cutting device, for example, glass, silicon, a metal, or a resin, is used as the base substrate 1. Surface treatment such as silanization or the like may be applied to the surface at at least the first-side surface of the base substrate 1 in order to enhance the adherence to the tissue section.

The contractible sheet 2 possesses thermal contractibility because it is formed of a thermoplastic resin such as polyvinyl chloride, polyester, or the like, and an adhesive B is applied on the surface thereof. The adhesive B is a UV-sensitive adhesive whose adhesive force is lost when irradiated with UV rays.

Following the cutting step S1, while the group of small pieces 1a is attached on the contractible sheet 2, they may be cleaned by means of ultrasonic waves in order to remove scraps of the base substrate 1 generated during cutting.

The contracting step S2 is performed by heating the contractible sheet 2. By doing so, as shown in (c) of FIG. 2, the contractible sheet 2 contracts in the direction along the surface thereof and adjacent small pieces 1a are brought into close contact with each other, thus closing the gaps A.

The transferring step S3 is performed by using an expandable sheet 3 that has the UV-sensitive adhesive B applied on the surface thereof, as with the contractible sheet 2, and that can be expanded in the direction along the surface thereof. Specifically, the adhesive force of the adhesive B is sufficiently reduced by irradiating the contractible sheet 2 with UV light, the surface of the expandable sheet 3 is subsequently attached to the group of small pieces 1a at second-side surfaces thereof, as shown in (d) of FIG. 2, and the contractible sheet 2 is then peeled off from the first-side surfaces of the group of small pieces 1a, as shown in (e) of FIG. 2. By doing so, it is possible to move the group of small pieces 1a on the contractible sheet 2 to the expandable sheet 3 while keeping them orderly arranged, and it is possible to fabricate a substrate sheet 10 including the group of small pieces 1a orderly arranged on the expandable sheet 3 without the gaps A therebetween.

As described above, with this embodiment, there is an advantage in that it is not necessary to perform the task of dividing the base substrate 1 into the group of small pieces 1a along the grooves, which is, in the related art, manually performed by an operator by using a glass cutter, and that the group of small pieces 1a can be arrayed on the respective sheets 2 and 3 without the gaps A therebetween, requiring only a simple operation.

The substrate sheet 10 fabricated in this way is used as described below.

Figure 3A:
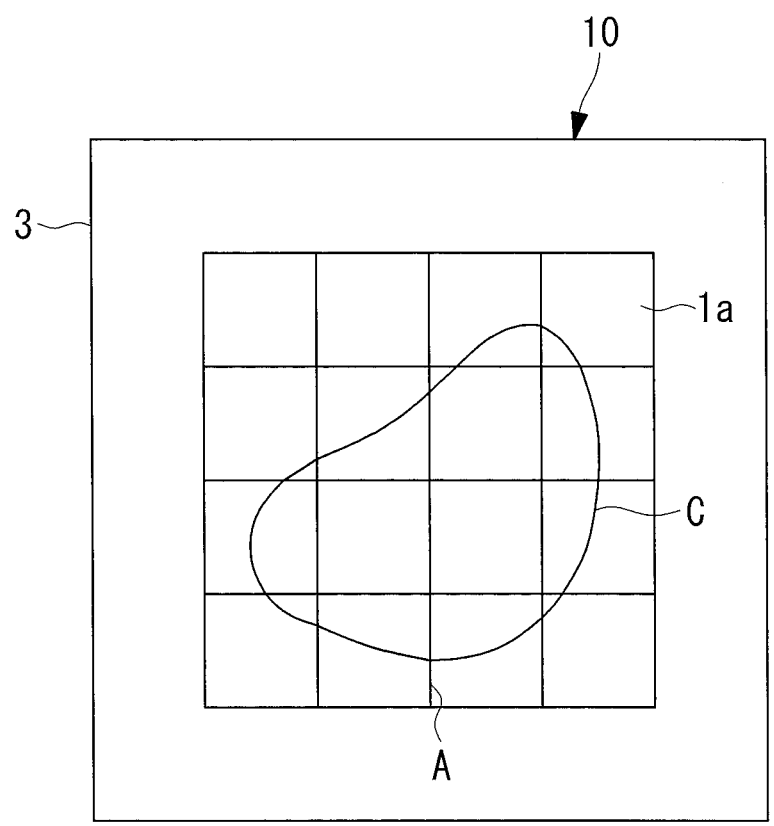
FIG. 3A is a diagram for explaining a method of using the substrate sheet, showing a state in which a tissue section is attached on the substrate sheet.
Figure 3B:
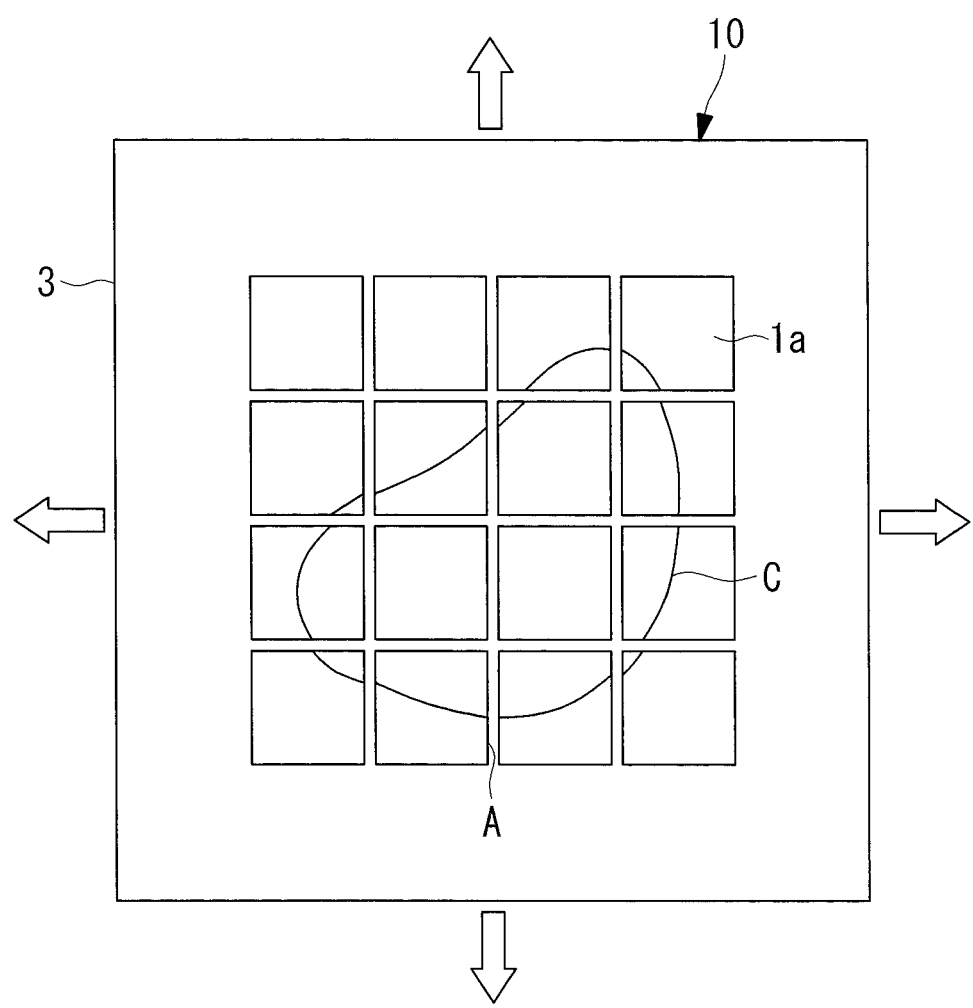
FIG. 3B is a diagram for explaining the method of using the substrate sheet, showing a state in which the tissue section is divided into segments.

First, as shown in FIG. 3A, a tissue section C is attached to the group of small pieces 1a in the substrate sheet 10, and the expandable sheet 3 is expanded in the direction along the surface thereof. By doing so, as shown in FIG. 3B, the small pieces 1a are separated from each other, thus forming the gaps A therebetween. At this time, because the tissue section C is also pulled in the direction along the surface, the tissue section C is divided along the grid-like gaps A into segments having substantially the same shapes as first-side surfaces of the small pieces 1a. By peeling off the small pieces 1a from the expandable sheet 3, a user can collect segments of the tissue section C together with these small pieces 1a.

At this time, if the tissue section is divided into segments by using a substrate in which the gaps A are already formed between the small pieces 1a, the size and shape of the segments become variable in accordance with the width of the gaps A. In contrast, in the case of the substrate 10 according to this embodiment designed for biological tissue, because the small pieces 1a are arrayed without the gaps A between each other, variability in the positions at which the tissue section C is divided is suppressed, and thus, the tissue section C is divided into segments having a substantially uniform size. Accordingly, there is an advantage in that the amount of biological tissue collected from the respective small pieces 1a can be made substantially uniform.

Note that, although a UV-sensitive adhesive is used as the adhesive B in this embodiment, alternatively, a temperature sensitive adhesive whose adhesive force is lost when heated or cooled may be used. In this case, the contractible sheet 2 is heated or cooled in the transferring step S3 instead of being irradiated with UV rays.

In this way also, the contractible sheet 2 can easily be peeled off from the group of small pieces 1a without disturbing the orderly arrangement of the group of small pieces 1a.

In addition, in this embodiment, an adhesive having a sufficiently greater adhesive force than the adhesive applied to the contractible sheet 2 may be used as an adhesive to be applied to the expandable sheet 3. In this way also, the contractible sheet 2 can easily be peeled off from the group of small pieces 1a while leaving the group of small pieces 1a on the surface of the expandable sheet 3, to which the small pieces 1a are attached with a greater adhesive force, without causing positional displacements thereof.

As such a contractible sheet 2 and expandable sheet 3, sheets having differing adhesive forces, such as an adhesive tape designed for dicing, a masking tape that protects a material surface, and so forth, can be used in combination.

For example, SV-224 (adhesive force: 1.1 N/20 mm) and UE-111AJ (adhesive force: 8.3 N/20 mm), which are made by Nitto Denko Co., can be used as the contractible sheet 2 and the expandable sheet 3, respectively. In addition, UE-1088JM (adhesive force: 6.0 N/20 mm) and UE-111AJ, which are made by Nitto Denko Co., can also be used as the contractible sheet 2 and the expandable sheet 3, respectively.

Figure 4:
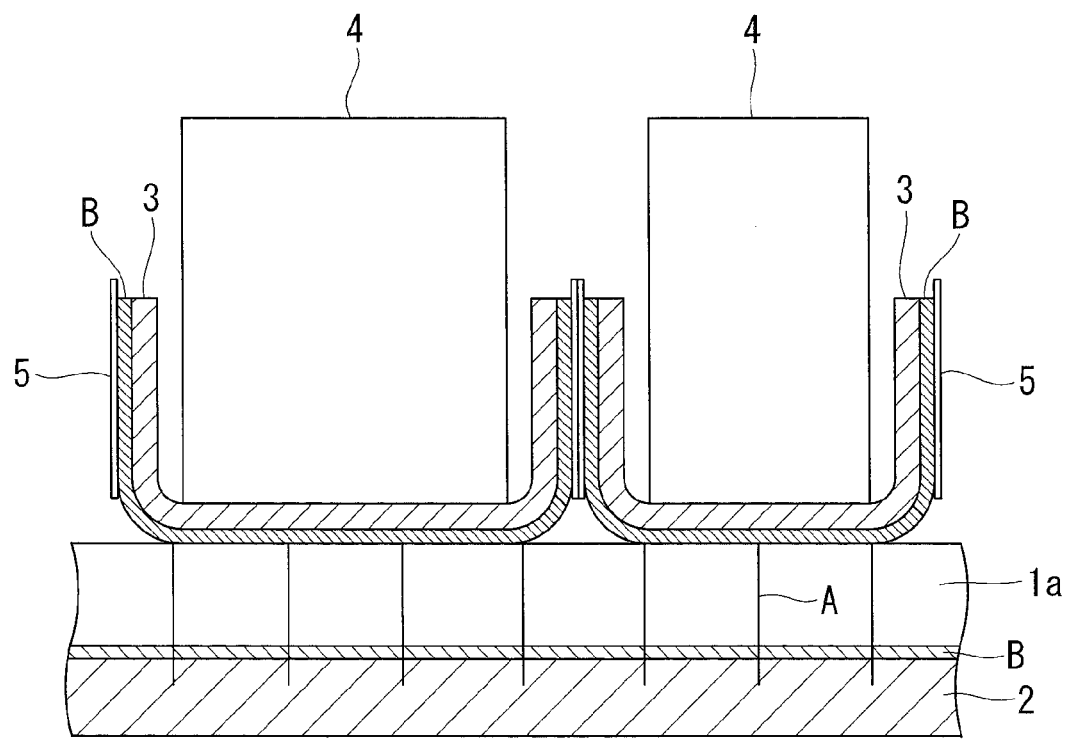
FIG. 4 is a schematic diagram showing a step in a modification of a transferring step in which the group of small pieces are transferred to a plurality of expandable sheets.

In addition, although a substrate to which a single tissue section can be attached is used as the base substrate 1 in this embodiment, alternatively, a substrate whose size allows for a plurality of tissue sections to be attached thereto may be used. In this case, the transferring step S3 is performed by, for example, as shown in FIG. 4, covering end surfaces of columnar pressing members 4 with the expandable sheets 3 and by pressing the end surfaces of the pressing members 4 against the group of small pieces 1a. By doing so, small pieces from different regions among the group of small pieces 1a are transferred to the plurality of expandable sheets 3. In order to facilitate the task, regions of the expandable sheets 3 other than the regions to be attached to the group of small pieces 1a may be protected by protective sheets 5 that do not attach to each other. As the protective sheets, it is preferable to use thin resin sheets, such as polypropylene sheets or the like.

By doing so, it is possible to easily fabricate substrate sheets 10 in which the group of small pieces 1a is arranged in an orderly fashion in arbitrary sizes and shapes in accordance with the sizes and shapes of the tissue sections to be attached to the substrate sheets 10. In addition, it suffices to perform the cutting step S1 once to fabricate the plurality of substrate sheets 10, and thus, the fabricating efficiency can be enhanced.

In addition, in this embodiment, a substrate sheet 10 in which the group of small pieces 1a is arranged in an orderly fashion on the contractible sheet 2 may be fabricated by using a sheet that can be expanded and contracted in a reversible manner in the direction along the surface thereof as the contractible sheet 2. A sheet formed of an elastic material, for example, rubber or the like, is used as the contractible sheet 2.

In this case, in the cutting step S1, the base substrate 1 is cut in a state in which the contractible sheet 2 is expanded by pulling it in the direction along the surface thereof. Subsequently, in the contracting step S2, the external force pulling the contractible sheet 2 is released, thus making the contractible sheet 2 contract due to a self-contraction force. Then, when dividing a tissue section, the contractible sheet 2 is expanded again by pulling it in the direction along the surface thereof.

By doing so, the substrate sheet 10 can be fabricated in an even simpler manner by omitting the transferring step S3.

Figure 5:
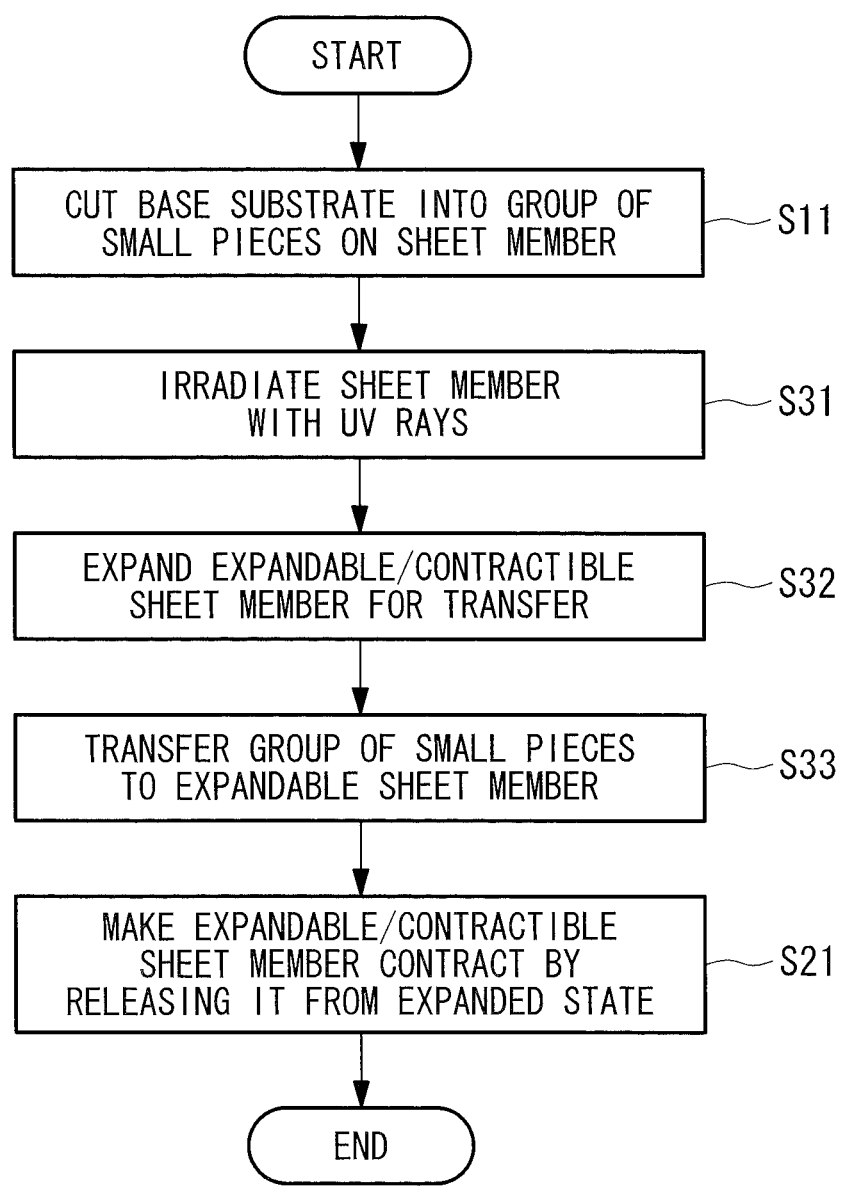
FIG. 5 is a flowchart showing a modification of the substrate-sheet fabricating method according to the embodiment of the present invention.

In addition, although the transferring step S3 is performed after the contracting step S2 in this embodiment, alternatively, a contracting step S21 may be performed after transferring steps S31 to S33, as shown in FIG. 5.

In this case, the sheet member (first sheet member) used in a cutting step S11 is not particularly limited so long as the base substrate 1 can be attached thereto.

An expandable/contractible sheet member that possesses the property of contracting back to the original shape without plastically deforming when expanded up to a certain amount is used as a transferring sheet member (second sheet member) used in the transferring steps S31 to S33. In this case, by transferring the group of small pieces (Step S33) in the state in which the expandable/contractible sheet member is expanded (Step S32), in the contracting step S21, gaps between the group of small pieces can be closed by making the expandable/contractible sheet member contract merely by releasing the tensile force acting on the expandable/contractible sheet member. Here, as a means of expanding the expandable/contractible sheet member, it is possible to suitably use, for example, a wafer expander that is used when expanding spaces between chips after a semiconductor wafer is diced into chips.

Note that it suffices that the transferring sheet member be contractible as with the above-described contractible sheet 2. Suitable raw materials for such a contractible sheet member include resins used in semiconductor dicing tapes, such as polyvinyl chloride, polyolefin, polyethylene terephthalate, and so forth.

In addition, a UV-sensitive adhesive, which is generally used in semiconductor dicing tape, is suitably used as an adhesive to be applied to the expandable/contractible sheet member. In addition, as described above, the transfer of the group of small pieces 1a can also be facilitated by using an adhesive having a greater adhesive force than an adhesive applied to the sheet member used in the cutting step S11 as an adhesive to be applied to the expandable/contractible sheet member.

EXAMPLE

Next, an Example of the above-described embodiment will be described.

In this Example, a method shown in FIG. 5 will be described, in which the group of small pieces are transferred to the expandable/contractible sheet member (second sheet member) that is expanded in advance, and the spaces between the small pieces are closed by making the expandable/contractible sheet member contract by releasing it from the expanded state after the transfer.

First, after washing with water, an 18-mm square cover glass having a thickness of 0.13 mm to 0.17 mm (made by Matsunami Glass Ind., Ltd.) was attached to a dicing tape (UE-111AJ, made by Nitto Denko Co.) that served as the first sheet member, and was cut into a group of small pieces with spaces of about 1 mm therebetween by using a dicing saw. By doing so, the cover glass was diced so that each side thereof was divided into 19 pieces. The cutting margin formed between the small pieces at this time was about 80 μm.

Next, the adhesive force of the adhesive applied to the first sheet member was reduced by irradiating the first sheet member with UV rays. A UV light-emitting-diode light source formed of ZUV-C10 (a controller made by Omron Co.) and ZUV-H10 (an LED head made by Omron Co.) was used as a light source for the UV rays. At this time, the output power of the UV rays was 150 mW at a wavelength of 365 nm. The UV rays were radiated at 100% output power for 60 seconds by moving the head at the back side of the first sheet member so that all small pieces in the group were uniformly irradiated with the UV rays. Furthermore, polyethylene sheets were attached to portions of the surface of the first sheet member where the group of small pieces was not attached, thus providing protection so as not to expose the portions other than the portions to which the group of small pieces was attached.

Next, a dicing tape (UE-111AJ) that serves as the second sheet member was expanded by using a wafer expander and was held in the expanded state. At this time, the second sheet member was expanded about 6% in the surface direction. Subsequently, the first sheet member in which the adhesive force of the adhesive had been reduced was placed over the second sheet member at the center thereof so as to sandwich the group of small pieces with the second sheet member, and the group of small pieces was sufficiently attached to the second sheet member by rolling a rubber roller on the back side of the first sheet member. Next, the group of small pieces was transferred to the second sheet member by slowly peeling off the first sheet member.

Subsequently, the second sheet member was made to contract by releasing it from the expanded state by removing the second sheet member, to which the group of small pieces had been transferred, from the wafer expander. Then, when the overall size of the group of small pieces that was arranged in an orderly fashion in the two axial directions was measured, the size thereof was 16.85-mm square. In other words, the gap between the small pieces was about 16 μm. The above experiment confirmed that, with the substrate-sheet fabricating method according to the present invention, the group of small pieces can be arranged in an orderly fashion with sufficiently small gaps therebetween.

REFERENCE SIGNS LIST 1 base substrate
1a small pieces
2 contractible sheet (first sheet member)
3 expandable sheet (second sheet member)
4 pressing member
5 protective sheet
10 substrate sheet
S1, S11 cutting step
S2, S21 contracting step S3, S31, S32, S33 transferring step
A gap
B adhesive

The invention claimed is:

1. A substrate-sheet fabricating method comprising:
cutting into a group of small pieces a base substrate whose first-side surface is attached to a first sheet member;
after the cutting the base substrate, transferring the group of small pieces to a second sheet member by attaching the second sheet member, which can be contracted in the direction along a surface thereof, to second-side surfaces of the group of small pieces and by peeling off the first sheet member from the first-side surfaces of the group of small pieces; and
after the transferring the group of small pieces, making the second sheet member contract in the direction along the surface thereof.

2. The substrate-sheet fabricating method according to claim 1,
wherein the second sheet member can be expanded in the direction along the surface,
the transferring includes transferring the group of small pieces in a state in which the second sheet member is expanded, and
the making includes releasing a tensile force acting on the second sheet member in the direction along the surface thereof.

3. The substrate-sheet fabricating method according to claim 1,
wherein the second sheet member possesses thermal contractibility, and
the making includes heating the second sheet member.

4. The substrate-sheet fabricating method according to claim 1,
wherein the base substrate is attached to the first sheet member by means of a UV-sensitive adhesive whose adhesive force decreases when irradiated with UV rays; and
the transferring includes irradiating the first sheet member with UV rays.

5. The substrate-sheet fabricating method according to claim 1,
wherein the base substrate is attached to the first sheet member by means of a temperature sensitive adhesive whose adhesive force decreases when subjected to a temperature change, and
the transferring includes heating or cooling the first sheet member.

6. The substrate-sheet fabricating method according to claim 1, wherein, the transferring includes attaching the second sheet member to the second-side surfaces of the group of small pieces by means of a greater adhesive force than that attaching the first sheet member.

7. The substrate-sheet fabricating method according to claim 1,
wherein a plurality of second sheet members are employed, and
the transferring includes transferring small pieces from different regions in the group of small pieces to the plurality of second sheet members.

8. A substrate-sheet fabricating method comprising:
cutting into a group of small pieces a base substrate whose first-side surface is attached to a first sheet member that can be contracted in the direction along a surface thereof;
after the cutting the base substrate, making the first sheet member contract in the direction along the surface thereof; and
after the making the first sheet member contract, transferring the group of small pieces to a second sheet member by attaching the second sheet member to second-side surfaces of the group of small pieces and by peeling off the first sheet member from the first-side surfaces of the group of small pieces.

9. The substrate-sheet fabricating method according to claim 8,
wherein the first sheet member can be expanded in the direction along the surface thereof,
the cutting includes cutting the base substrate in a state in which the first sheet member is expanded, and
the making includes releasing a tensile force acting on the first sheet member in the direction along the surface thereof.

10. The substrate-sheet fabricating method according to claim 8,
wherein the first sheet member possesses thermal contractibility, and
the making includes heating the first sheet member contract.

11. The substrate-sheet fabricating method according to claim 8,
wherein the base substrate is attached to the first sheet member by means of a UV-sensitive adhesive whose adhesive force decreases when irradiated with UV rays; and
the transferring includes peeling off the first sheet member from the first-side surfaces of the group of small pieces by irradiating the first sheet member with UV rays.

12. The substrate-sheet fabricating method according to claim 8,
wherein the base substrate is attached to the first sheet member by means of a temperature sensitive adhesive whose adhesive force decreases when subjected to a temperature change, and
the transferring includes peeling off the first sheet member from the first-side surfaces of the group of small pieces by heating or cooling the first sheet member.

13. The substrate-sheet fabricating method according to claim 8, wherein, the transferring includes attaching the second sheet member to the second-side surfaces of the group of small pieces by means of a greater adhesive force than that attaching the first sheet member.

14. The substrate-sheet fabricating method according to claim 8,
wherein a plurality of second sheet members are employed, and
the transferring includes transferring small pieces from different regions in the group of small pieces to the plurality of second sheet members.

15. A substrate-sheet fabricating method comprising:
cutting into a group of small pieces a base substrate whose first-side surface is attached to a first sheet member that can be contracted in the direction along a surface thereof; and
after the cutting the base substrate, making the first sheet member contract in the direction along the surface thereof.

16. The substrate-sheet fabricating method according to claim 15, wherein the first sheet member can be expanded in the direction along the surface thereof,
the cutting includes cutting the base substrate in a state in which the first sheet member is expanded, and the making includes releasing a tensile force acting on the first sheet member in the direction along the surface thereof.

17. The substrate-sheet fabricating method according to claim 15, wherein the first sheet member possesses thermal contractibility, and the making includes heating the first sheet member.

\* \* \* \* \*